United States Patent [19]

Feeman

[11] Patent Number: 4,830,788

[45] Date of Patent: May 16, 1989

[54] PROCESS FOR PREPARATION OF SUBSTITUTED-AMINOMETHYLPHOSPHONIC ACIDS

[75] Inventor: James F. Feeman, Wyomissing, Pa.

[73] Assignee: Crompton & Knowles Corporation, Stamford, Conn.

[21] Appl. No.: 123,222

[22] Filed: Nov. 20, 1987

[51] Int. Cl.$^4$ ................................................ C07F 9/38
[52] U.S. Cl. ...................... 260/512.5 E; 260/502.5 D
[58] Field of Search ................. 260/502.5 E, 502.5 D, 260/502.5 F

[56] References Cited

U.S. PATENT DOCUMENTS

| | | | |
|---|---|---|---|
| 2,304,156 | 12/1942 | Engelmann et al. | 260/543 P |
| 2,328,358 | 8/1943 | Pitman | 260/543 P |
| 3,288,846 | 11/1966 | Irani et al. | 260/502.5 E |
| 4,368,162 | 1/1983 | Maier | 260/502.5 E |
| 4,409,151 | 10/1983 | Redmove et al. | 260/502.5 E |
| 4,422,982 | 12/1983 | Subramanian | 260/502.5 F |
| 4,578,224 | 3/1986 | Bayer et al. | 260/502.5 F |

OTHER PUBLICATIONS

Vogel "Practical Organic Chemistry" 3rd ed. (1957), pp. 131 and 132.

*Primary Examiner*—J. E. Evans
*Attorney, Agent, or Firm*—Bernard Francis Crowe

[57] ABSTRACT

A process is disclosed for the preparation of N-substituted aminomethylphosphonic acids, particularly methylaminomethylphosphonic acid, in high yield and purity with related low production cost using conventional equipment, which comprises the steps of (a) reacting an N-substituted amide with paraformaldehyde in a low molecular weight carboxylic acid to form the N-methylol derivative, (b) reacting the N-methylolamide with PCl$_3$ in excess low molecular weight carboxylic acid and heating to form the phosphonomethyl derivative, (c) hydrolyzing acid chloride and acid anhydride with water, (d) distilling off the low-molecular weight carboxylic acid, (e) hydrolyzing the N-acyl group with water and strong acid catalyst, (f) adding low molecular weight alcohol to crystallize the N-substituted-aminomethylphosphonic acid and (g) filtering, and washing the product.

13 Claims, No Drawings

PROCESS FOR PREPARATION OF SUBSTITUTED-AMINOMETHYLPHOSPHONIC ACIDS

This invention relates to a new process for preparing substituted-aminomethyl-phosphonic acids and particularly methylaminomethylphosphonic acid that results in high yield and purity with low cost.

The novel process provides compounds having utility as intermediates for dyes which are applicable to cellulosic and other natural fibers, as herbicides and as fire retardants when applied to cellulosic materials.

The process has advantages over prior processes in that it operates at atmospheric pressures in conventional industrial equipment using inexpensive solvents and produces pure crystalline product in high yield at reasonable cost.

Some of the substituted-aminomethylphosphonic acids that can be made by this process are known compounds which have interesting herbicidal and fireproofing applications; see, e.g. U.S.S.R. No. SU 1,074,886 (Chemical Abstracts, 100, 19374C (1984) and Ger. Offen. No. 2,848,869 (Chemical Abstracts, 93, 39529Z (1980). They have also recently been found to be especially valuable as low-cost intermediates for production of reactive dyes which contain phosphonic acid groups as disclosed in my simultaneously filed applications: "N-Alkyl-N-(aminophenylsulfonyl)-aminoalkylphosphonic Acids", "Triazinyl Reactive Dyes Having Two or More Phosphonic Groups", "Disazo Reactive Dyes Containing Phosphonic Acid Groups", and "Disazo Reactive Dyes for Cellulosic Fibers". The dyes of these applications are applicable to cellulosic textile materials by the processes of U.S. Pat. Nos. 4,134,722 and 4,139,345.

Although several processes for production of some of these substituted-aminomethyl-phosphonic acids have been patented or published otherwise, all of them have one or more disadvantages which hinder their use for commercial production.

In U.S. Pat. No. 2,328,358, N-methyl-N-methylolstearamide is reacted with PCl₃ to give the corresponding phosphonylchloride, which upon treatment with dilute hydrochloric acid affords N-methyl-stearamidomethylphosphonic acid,

$$C_{17}H_{35}-CON-CH_2PO_3H_2,$$
$$|$$
$$CH_3$$

CH₂PO₃H₂,
which is then hydrolyzed to methylaminomethylphosphonic acid. In addition to excessively lengthy reaction times, use of stearamide, or other high-molecular-weight amide, adds correspondingly high cost, excessive reaction volume and bulky by-product which is undesirable, requiring disposal or expensive recovery.

The process of U.S. Pat. No. 3,907,652 involves reaction of methylamine, formaldehyde and phosphorus acid (cf. Journal of Organic Chemistry 31, 1603 (1966)) followed by oxidative electrolysis of the bis-(phosphonomethyl)-methylamine,

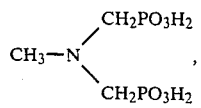

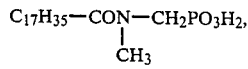

to remove one phosphonomethyl group leaving methylaminomethylphosphonic acid. Special equipment is required for the latter reaction which is done in strong aqueous acid.

In U.S. Pat. No. 4,351,779, L. Maier claims a process comprising heating at 20°-150°, trimethylhexahydro-s-triazine with excess secondary dialkyl phosphite to obtain methylaminomethylphosphonic acid diester. Unfortunately the secondary dialkyl phosphite is an expensive source of phosphorus making this process relatively uneconomical. Also, the methylaminomethylphosphonic acid is produced from the intermediate diester by either precipitation from ether solution with gaseous HCl, or pyrolyzed at high temperatures (230°-240° C.), neither of which methods is industrially attractive.

Another process patented by L. Maier (U.S. Pat. No. 4,160,779) produces methylaminomethylphosphonic acid by reacting bis(chloromethyl)phosphonic acid in aqueous ammonia at elevated temperature (150° C.) and 80 bars pressure for seven hours. This requires a high pressure autoclave, an expensive piece of equipment. Also, purification of the crude product is effected by passing it as an aqueous solution over an acid ion exchanger and evaporating the eluate.

Bayer, et al., in U.S. Pat. No. 4,578,224 disclose and claim a method for preparation of salts of N-phosphonomethylglycine which includes some similar steps to those of the present invention; however, they include only hydantoin or a 3-substituted hydantoin as starting materials, which are cyclic compounds containing two N atoms in the ring, i.e.

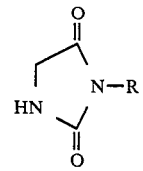

Straight chain aliphatic amides, saturated carbocyclic amides, or arylaliphatic amides in contrast, are the starting materials of this invention. In the Bayer, et al., patent examples, while yields of 38-72% of theory of desired product are indicated, the lower yield represents isolated crystalline product obtained by a multi-step purification not included in their claimed process and the higher yield represents an HPLC analysis of crude product. The process of the present invention gives crystalline product of high yield and purity directly from the reaction mixture without further purification/isolation steps. Other important differences are also obvious in the order of the steps, and in the manner in which they are effected, when the processes are compared in detail.

Tyka and Hägele, SYNTHESIS, (3) 218-19 (1984) (Chemical Abstracts, 101, 91052m (1984)), describe a laboratory procedure for synthesis of N-alkylaminomethanephosphonic acids. They review the two general synthetic routes leading to N-alkylaminomethanephosphonic acids, i.e. (1) Mannich-type reactions of primary amines with formaldehyde and phosphorus acid and (2) condensation reactions of primary amines with chloromethanephosphonic acids. They state that the first method yields mixtures of mono- and bis-methanephosphonic acids, while the second method requires long reaction times and ion exchange purification, all of which are undesirable. Their method is by reaction of N-alkyl-N-hydroxymethyl-formamides with phosphorus trichloride in glacial acetic acid solution. However, their process requires preparation and isolation of N-alkyl-N-hydroxymethylformamide. Chloroform, a toxic solvent, is used to separate this intermediate. The subsequent step requires addition of this intermediate, as a solution in acetic acid to phosphorus trichloride, the reverse of the present invention. Subsequent isolation and purification steps use propylene oxide and acetone, highly flammable, low-boiling solvents which are hazardous in large scale operations. With regard to the preparation of N-hydroxymethyl amides they also state that "Unfortunately, we were not able to obtain N-hydroxymethylamides in yields higher than 30% using the method" of H. Böhme, et al., Chem. Ber. 94, 1879 (1961), in which N-alkylacetamides or N-alkyl benzamides and paraformaldehyde are reacted in the presence of dry potassium carbonate at high temperatures. Contrary to the findings of Böhme and of Tyka and Hägele, I have now discovered that isolation of the N-hydroxymethylamide is not necessary and that N-methylacetamide in the process of the present invention gives yields of N-methylaminomethylphosphonic acid in excess of 75% overall.

SUMMARY OF THE INVENTION

It has now been discovered that N-alkyl-,N-aralkyl-, and N-cycloalkyl-amino-methylphosphonic acids can be produced in good yields and isolated as crystalline solids by a. reacting an amide, R-NH-COR$_1$, with paraformaldehyde in the presence of a low molecular weight carboxylic acid and sufficient low molecular weight acid anhydride to react with all water in the paraformaldehyde, at a temperature and for a sufficient period of time to form the N-methylol derivative of a high percentage of the amide having the formula

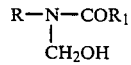

or its low molecular weight carboxylic ester,

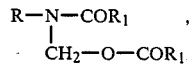

wherein R is alkyl, aralkyl or cycloalkyl having 1–18 carbon atoms and R$_1$ is lower alkyl having 1–4 carbon atoms, b. reacting the N-methylol-amide or its ester with phosphorus trichloride in the presence of excess low-molecular weight carboxylic acid, and heating said reaction for a sufficient time to eliminate substantially all of the hydrogen chloride formed and complete formation of the phosphonomethyl derivative of the amide, c. adding sufficient water to hydrolyze acid chloride and acid anhydride by-products, d. recovering substantially all of the low-molecular weight carboxylic acid by distillation, e. adding sufficient water and a strong mineral acid catalyst to hydrolyze the acyl group of the N-alkyl-,N-aralkyl- or N-cycloalkyl-N-phosphonomethylacylamide, f. adding a low molecular weight alcohol to crystallize the N-alkyl-, N-aralkyl- or N-cycloalkyl-aminomethylphosphonic acid, and g. filtering the product and washing with low molecular weight alcohol to produce crystalline N-alkyl-,N-aralykl- or N-cycloalkyl-aminomethylphosphonic acid in high yield and purity.

Suitable amides for use in the process include formamides, acetamides, propionamides and butyramides of alkyl amines such as e.g. methylamine, ethylamine, propylamine, butylamine, amylamine, hexylamine, heptylamine, octylamine, nonylamine, decylamine, octadecylamine, of aralkylamines such as benzylamine or 2-phenylethylamine, or of cycloalkylamines such as cyclohexylamine, cyclopentylamine, cycloheptylamine or cyclooctylamine.

The preferred amide, primarily because of cost considerations is N-methylacetamide.

Suitable low molecular weight carboxylic acids include acetic acid, formic acid, propionic acid and butyric acid, of which acetic acid is preferred because of cost and availability. This acid may be used in excess or stoichiometrically.

Paraformaldehyde is used in this process because it contains minimal water. Commercially available material is nominally 91% CH$_2$O, with the remaining 9% being water. Acid anhydride is employed in the methylolation step to react with all water present and effectively eliminate it from the reaction.

Phosphorus trichloride is preferred as the lowest cost source of phosphorus, although phosphorus tribromide could also be used.

The preferred mineral acid in step (e) is sulfuric acid, however other acids such as hydrochloric, hydriodic, phosphoric or other strong protic acids could be used.

Low molecular weight alcohols suitable for use in steps (f) and (g) are methanol, ethanol, propanol, and isopropanol, Methanol is preferred because of its low cost and is especially preferred for isolation of methylaminomethylphosphonic acid, since it gives excellent yields of high purity product as a result of the low solubility of the product in it, while impurities are more soluble in it.

The overall reaction sequence for the process of this invention is believed to be as follows, using the preferred starting materials.

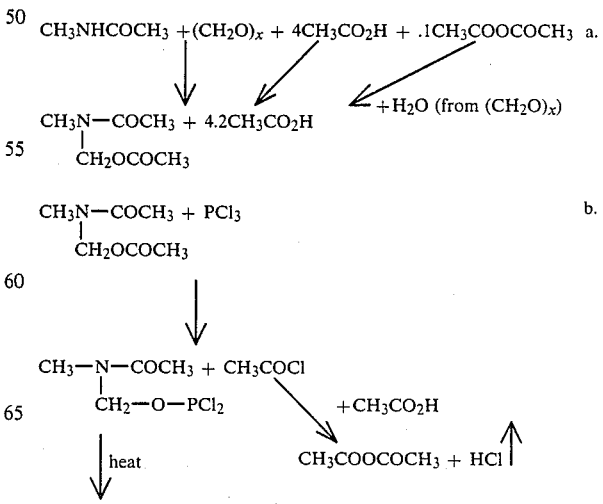

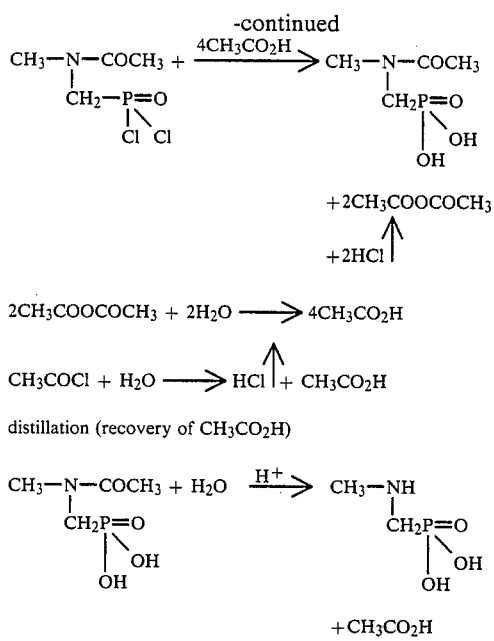

$$2CH_3COOCOCH_3 + 2H_2O \longrightarrow 4CH_3CO_2H$$

$$CH_3COCl + H_2O \longrightarrow HCl\uparrow + CH_3CO_2H$$

distillation (recovery of $CH_3CO_2H$)    d.

$$\begin{array}{c} CH_3-N-COCH_3 \\ | \\ CH_2P=O \\ \diagdown \\ |\phantom{x}OH \\ OH \end{array} + H_2O \xrightarrow{H^+} \begin{array}{c} CH_3-NH \\ | \\ CH_2P=O \\ \diagdown \\ |\phantom{x}OH \\ OH \end{array}$$ e.

$$+ CH_3CO_2H$$

In the process of this invention the main reactants are used in approximate equimolar amounts: N-methylacetamide and paraformaldehyde are preferably present in 1:1 stoichiometric ratio while phosphorus trichloride is used in equimolar to about 4% excess. Variations from this have proportional effects on yield obtained.

The low-molecular weight carboxylic acid is used in excess, preferably according to the stoichiometry given in the overall reaction sequence. Larger excesses are not harmful, but are not cost-effective.

Step (a) is conducted at temperatures from about 100° C. to, preferably, near the boiling point of acetic acid, 118° C.

In Step (b) the phosphorus trichloride is added at temperatures from normal room temperature (20°–25°) to about 70° C.

Generation of acetyl chloride occurs during this step; it subsequently partially reacts with acetic acid to form acetic anhydride and hydrogen chloride, partially escapes with evolved hydrogen chloride, and partially is hydrolyzed by water added in Step (c). Alternatively the acetyl chloride which is formed may be removed by distillation when it is formed or immediately thereafter.

During the heating period in Step (b) the initially formed phosphate ester intermediate rearranges to the phosphonate structure. Then the dichlorophosphonate reacts with acetic acid, liberating hydrogen chloride and forming the phosphonomethyl group. The acetic acid is simultaneously converted to acetic anhydride. The temperature is gradually raised from 70° to temperatures in excess of 100° C. to effect these reactions. It appears preferable to attain temperatures of 130°–135° C. to obtain maximum yield of product.

Water is added in Step (c) in sufficient amount to hydrolyze all acetic anhydride and acetyl chloride present in the reaction mixture. Large excesses of water do not lower the yield, but are not necessary and must be removed by distillation in Step (d).

Atmospheric distillation or distillation under reduced pressure may be used in Step (d). The acetic acid/water generated in Step (c), plus any excess acetic acid used in the initial steps, must be substantially removed at this step in order that higher yield of product may be attained in Step (g). Additional acetic acid present when the low-molecular weight alcohol is added results in higher solubility of the product in the solvent mixture and consequent loss of product in the filtrate.

Hydrolysis of the acyl group in Step (e) is carried out with water and a strong acid, present in catalytic amount. The water should be present in only slightly over stoichiometric amount so that a reflux temperature of 115°–117° C. is attained. More water lowers the reflux temperature, which in turn lengthens time of hydrolysis, and also is present in the final crystallization, lowering yield, since the product is highly soluble in water.

EXAMPLE 1

Preparation of Methylamino-methylphosphonic Acid

In a 1000 ml round-bottom flask equipped with a stirrer, thermometer, electric mantle and condenser, connected to a water-trap for absorbing evolved hydrochloric acid, 73 g. of N-methylacetamide, 222 g. of acetic acid, 25 g. of acetic anhydride, and 33 g. of 91% paraformaldehyde were heated to 116° C. and held at that temperature for 30 minutes resulting in a clear solution. After cooling the flask contents to 25° C., 142 g. of phosphorus trichloride was added dropwise during 24 minutes with the temperature rising to 65°–69° C. Near the end of the PCl$_3$ addition, HCl began to evolve and acetyl chloride refluxed. Heat was applied to maintain the temperature at 59°–70° C. for forty-five minutes and then gradually increase it to 130° C., during three hours. HCl evolution was vigorous for the first two hours of this heating period, then slowed and eventually nearly stopped. Acetyl chloride refluxed throughout this period, also. The reaction was cooled to 100° C. with a cold water bath. Water (35 g.) was cautiously added to hydrolyze acetyl chloride and acetic anhydride, formed as by-products. Some of the acetic acid which formed, plus that present in excess as solvent, was removed by distillation at atmospheric pressure (179 g. was recovered, containing 2.1 g. of water).

To the residual oil in the flask was added a solution of 2 g. of 93% sulfuric acid and 37 g. of water. The clear solution was heated at reflux (115°–116° C.) for six hours. Upon cooling to 90° C. product began to crystallize out. Addition of 150 ml. of methanol and further cooling to 20° C. resulted in a slurry of crystalline product. It was filtered, washed on the Buchner funnel with 50 ml. of methanol, and dried, giving 95.4 g. of colorless crystals, (76.3% of theory) which melted at 280°–288° C. (literature 272°–274° C.; 274.5°–275.5° C.).

When the above procedure was repeated using 59 g. of N-methylformamide in place of the 73 g. of N-methylacetamide, 47 g. of crystalline methylaminomethylphosphonic acid was obtained.

EXAMPLE 2

Preparation of n-Butylamino-methylphosphonic Acid

In a 1000 ml. round-bottom flask equipped with a stirrer, thermometer, electric heating mantle and condenser, connected to a water-trap for absorbing evolved hydrochloric acid, was placed 126 g. of acetic anhydride. The temperature was raised to 80° C. and 73 g. of 96% n-butylamine (technical grade from Aldrich Chemical Company, Inc.) was dropping in during 37 minutes with the temperature rising to 112° C. The solution of N-n-butylacetamide was cooled to 25° C. by means of a water bath. Acetic acid (163 g.) and paraformaldehyde (33 g. - 91%) were then added and the mixture heated to 111°–114° C. for 30 minutes. The solution which formed was cooled to 25° C.

Phosphorus trichloride (142 g.) was added during 20 minutes with temperature of the reaction rising to 65° and maintained at 62°–65° C. with water-bath cooling as needed. Near the end of the addition, evolution of HCl started and acetyl chloride refluxed. The temperature was gradually increased during the next six hours to 137° C. during which HCl evolution increased and finally stopped.

The reaction was cooled with a water-bath to 100° C. Water (35 g.) was cautiously added at 100°–110° C. in 10 minutes to hydrolyze acetyl chloride and acetic anhydride which formed as by-products. Acetic acid was recovered by distillation at atmospheric pressure (213 g. containing 0.17% of water).

After cooling to 100° C., a mixture of 2 g. 93% sulfuric acid and 39 g. of water was added. The resultant solution was refluxed at 116°–117° for 18.5 hours, hydrolyzing the N-acetyl group. The solution was cooled to 70° C. and 150 ml. of methanol added, followed by further cooling to 20° C. and stirring for several hours. The crystalline n-Butylaminomethyl-phosphonic acid was filtered, washed with 50 ml. of methanol, and dried. The yield was 93.8 g. (58.5% of theory) of colorless crystals which melted at 242°–244° C. (literature m.p. 235°–237°; 248°–250°).

EXAMPLE 3

Preparation of Isopropylaminomethylphosphonic Acid

In Example 2, while otherwise proceeding as described, but substituting an equimolar quantity of isopropylamine for the n-butylamine, and isopropanol for the methanol, isopropylaminomethylphosphonic acid was obtained having melting points 267°–269° C.

EXAMPLE 4

Preparation of Ethylamino methylphosphonic Acid

In Example 1, while otherwise proceeding as described, but substituting 87 g. of N-ethylacetamide for the 73 g. of N-methylacetamide, ethylaminomethylphosphonic acid was obtained as a crystalline solid in 49% yield which melted at 279°–284° C. (literature m.p. 273°–275° C.).

EXAMPLE 5

Preparation of n-Octylaminomethylphosphonc Acid

In Example 2, while otherwise proceeding as described, but substituting 129.3 g. of n-octylamine for the 73 g. of n-butylamine, n-octylaminomethylphosphonic acid was obtained in 61% yield (136 g.) as a colorless crystalline solid having melting point 264°–266° C.

EXAMPLE 6

Preparation of n-Octadecylaminomethylphosphonic Acid

In Example 2, while otherwise proceeding as described, but substituting 27 g. of octadecylamine for the 73 g. of n-butylamine and adjusting all other quantities of materials to 0.1 of the amounts given, n-octadecylaminomethylphosphonic acid was obtained in 99% of theoretical yield (35 g.) as an offwhite solid which melted at 108°–112° C.

EXAMPLE 7

Preparation of Cyclohexylaminomethylphosphonic Acid

In Example 2, while otherwise proceeding as described, but substituting 99 g. of cyclohexylamine for the 73 g. of n-butylamine, and replacing the methanol with ethanol, cyclohexylaminomethylphosphonic acid was obtained as a colorless solid which melted at 279°–284° C.

EXAMPLE 8

Preparation of 2-Phenylethylaminomethylphosphonic Acid

In Example 2, while otherwise proceeding as described, but substituting 124 g. of 2-phenylethylamine for the 73 g. of n-butylamine, and replacing the methanol with ethanol, 2-phenylethylaminomethylphosphonic acid was obtained in 77% of theoretical yield (165.5 g.) as an off-white crystalline solid which melted at 148°–150° C.

What is claimed is:

1. A process for the preparation of alkyl-, aralkyl- or cycloalkyl-aminomethylphosphonic acids which comprises the steps of:

a. reacting an amide, R-NH-COR$_1$, with paraformaldehyde in the presence of a low molecular weight carboxylic acid and sufficient low molecular weight acid anhydride to react with all water in the paraformaldehyde, at a temperature and for a sufficient period of time to form the N-methylol derivative of a high percentage of the amide having the formula

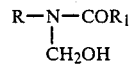

or its low molecular weight carboxylic ester,

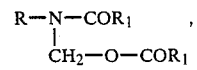

wherein R is alkyl aralkyl or cycloalkyl having 1–18 carbon atoms and R$_1$ is lower alkyl having 1–4 carbon atoms, b. reacting the N-methylol-amide or its ester with phosphorus trichloride in the presence of excess low-molecular weight carboxylic acid, and heating said reaction for a sufficient time to eliminate substantially all of the hydrogen chloride formed and complete formation of the phosphonomethy derivative of the amide, c. adding sufficient water to hydrolyze acid chloride and acid anhydride by-products, d. recovering substantially all of the low-molecular weight carboxylic acid by distillation, e. adding sufficient water and a strong mineral acid catalyst to hydrolyze the acyl group of the N-alkyl-, N-aralkyl- or N-cycloalkyl-N-phosphonomethylacylamide, f. adding a low molecular weight alcohol to crystallize the N-alkyl-, N-aralkyl- or N-cycloalkylaminemethylphosphonic acid, and g. filtering the product and washing with low molecular weight alcohol to produce crystalline N-alkyl- , N-aralkyl- or N-cycloalkylaminomethylphosphonic acid in high yield and purity.

2. The process of claim 1 wherein the amide is a formamide, acetamide, propionamide or butyramide of an alkyl, aralkyl, or cycloalkyl primary amine including methylamine, ethylamine, propylamine, butylamine, amylamine, hexylamine, cyclohexylamine, heptylamine, cycloheptylamine, octylamine, cyclooctylamine, 2-phenylethylamine, benzylamine, nonylamine, decylamine, octadecylamine and cyclopentylamine.

3. The process of claim 1 wherein the amdie is N-methylacetamide, the low molecular weight carboxylic acid is acetic acid, the low molecular weight alcohol is methanol, the low molecular weight acid anhydride is acetic anhydride and the strong mineral acid catalyst is sulfuric acid.

4. The process of claim 1 wherein the amide, paraformaldehyde and phosphorus trichloride are present in approximately equimolecular amounts.

5. The process of claim 3 wherein the N-methylacetamide, paraformaldehyde and phosphorus trichloride are present in approximately equimolecular amounts.

6. The process of claim 3 wherein the N-methylacetamide and paraformaldehyde are present in equimolecular amount and the phosphorus trichloride is present in about 4% excess above equimolecular amount.

7. The process of claim 1 wherein the temperature in Step (a) is 100° C. to 118° C. . . . .

8. The process of claim 3 wherein the temperature in Step (a) is 100° C. to 118° C.

9. The process of claim 1 wherein the temperature of addition of phosphorus trichloride is from 20° C. to about 70° C. and the final reaction temperature is about 100° C. to 135° C.

10. The process of claim 3 wherein the temperature of addition of phosphorus chloride is from about 20° C. to about 70° C. and the final reaction temperature is about 100° C. to 135° C.

11. The process of claim 1 wherein in Step (d) the low molecular weight carboxylic acid is removed by distillation under atmospheric or reduced pressure.

12. The process of claim 3 wherein in Step (d) the acetic acid is removed by distillation under atmospheric or reduced pressure.

13. The process of claim 3 wherein in Step (e) water is present in only slightly over stoichiometric amount.

* * * * *